(12) United States Patent
Hopmann et al.

(10) Patent No.: US 7,112,608 B2
(45) Date of Patent: Sep. 26, 2006

(54) HYDROXYPHENYLUNDECANE, A PROCESS FOR THEIR PRODUCTION AND THEIR USE

(75) Inventors: Cordula Hopmann, Berlin (DE); Martin Knauf, Rapperswil (CH); Mark Brönstrup, Frankfurt (DE); Astrid Markus-Erb, Liederbach (DE); Luigi Toti, Hochheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/676,715

(22) Filed: Oct. 1, 2003

(65) Prior Publication Data

US 2004/0122092 A1 Jun. 24, 2004

Related U.S. Application Data

(60) Provisional application No. 60/439,629, filed on Jan. 13, 2003.

(30) Foreign Application Priority Data

Oct. 2, 2002 (EP) ................... 02022095

(51) Int. Cl.
*A61K 31/255* (2006.01)
*A61K 31/235* (2006.01)
*C07C 69/76* (2006.01)
*C07C 305/00* (2006.01)

(52) U.S. Cl. .................. 514/517; 514/543; 558/24; 558/32; 560/75

(58) Field of Classification Search ............... 514/543, 514/517; 558/24, 32; 560/75
See application file for complete search history.

(56) References Cited

FOREIGN PATENT DOCUMENTS

| GB | 2327674 | 2/1999 |
| WO | WO 98/04257 | 2/1998 |
| WO | WO 00/04023 | 1/2000 |
| WO | WO 01/23379 | 4/2001 |

OTHER PUBLICATIONS

Heinz Stolp, Microbial Ecology: Organisms, Habitats, Activities, Cambridge University Press (1988, pp. 173-181, vol. 180).
Jian Feng et al., Spinophilin Regulates the Formation and Function of Dendritic Spines, Proc. Natl. Acad. Sci. (2000, pp. 9287-9292, vol. 97).
Linda C. Hsieh-Wilson et al., Characterization of the Neuronal Targeting Protein Spinophilin and Its Interactions with Protein Phosphatase-1, Biochemistry (1999, pp. 4365-4373, vol. 38).
Thomas D. Brock et al., Biology of Microorganisms, Prentice Hall (1984, pp.238-247).
Yoshihiro Kumagae et al., Human c-Jun N-Terminal Kinase Expression and Activation in the Nervous System, Molecular Brain Res. (1999, pp. 10-17, vol. 67).
Remington Pharmaceutical Sciences (1985, pp. 1418).

*Primary Examiner*—Taylor Victor Oh
(74) *Attorney, Agent, or Firm*—Irving Newman

(57) ABSTRACT

The present invention relates to novel hydroxyphenylundecane derivatives of the formula (I),

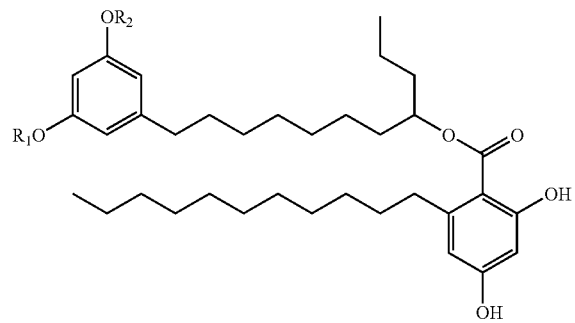

a method for the preparation of said compounds by cultivation of the fungus *Cryphonectria parasitica*, DSM 14453, and their use as pharmaceuticals, i.e. for the treatment of Alzheimer's Disease, Parkinson's Disease, Huntington's Diseases, stroke, psychosis and/or depressions.

10 Claims, No Drawings

HYDROXYPHENYLUNDECANE, A PROCESS FOR THEIR PRODUCTION AND THEIR USE

The present application claims the benefit of the following non-provisional application filed on Jan. 13, 2003: 60/439,629.

BACKGROUND OF THE INVENTION

1. Field of the Invention

The present invention relates to novel hydroxyphenylundecane derivatives, a method for the preparation of said compounds and their use as pharmaceuticals, i.e. for the treatment of Alzheimer's Disease, Parkinson's Disease, Huntington's Diseases, stroke, psychosis and/or depressions.

2. Description of the Art

Differential expression and localization of c-Jun N-terminal kinases (JNKs) in the human brain reflects transduction of a variety of extracellular stimuli to selective cellular responses. Of the 3 JNKs, JNK1 and JNK2 are widely distributed in tissues and JNK3 is predominantly restricted to brain where it is expressed in neurons. The c-Jun N-terminal Kinase (JNK) pathway leading to c-Jun phosphorylation plays a causal role in apoptosis of isolated primary embryonic neurons and of multiple neuronal cell lines following a wide variety of stimuli. Activation of this pathway is suggested to contribute to the neuronal atrophy and death that is associated with neurodegenerative pathological conditions including Alzheimer's Disease, Parkinson's Disease, Huntington's Diseases and stroke (Kumagae et al., Mol. Brain Res. (1999), 67(1), 10–7). Inhibitors of JNK3 therefore should stop apoptosis and be useful for the treatment and/or prevention of the above mentioned diseases.

Protein phosphatase-1 (PP1) is a serine/threonine phosphatase that plays an important role in a variety of cellular processes, including muscle contraction, cell-cycle progression, and neurotransmission (Hsieh-Wilson et al., Biochemistry 1999, 38, 4365–4373). The localization and substrate specifity of PP1 are determined by a class of proteins known as targeting subunits. Targeting subunits restrict the otherwise broad specifity of the catalytic subunit ($PP1_c$) by directing the enzyme to discrete subcellular compartments and, in some cases, by modulating its activity toward particular substrates. Studies support the notion that spinophilin, a protein highly enriched in dendritic spines, functions as a neuronal targeting subunit of PP1. Spinophilin plays an important role in regulating the phosphorylation states of glutamate receptors in dendritic spines e.g. the glutamat receptor AMPA (α-amino-3-hydroxy-5-methyl-4-isoxazolepropionic acid) by anchoring PP1 in the proximity of these receptors (Jiang Feng et al., Proc. Natl. Acad. Sci. USA 2000, 97, 9287–9292). In the absence of spinophilin, AMPA receptors are no longer subjected to down-regulation by PP1, which results in more persistent AMPA receptor currents. Dysregulation of glutamate receptor currents leads to specific changes in neuronal circuits, which may lead e.g. to long-term depression. Molecules that interfere with the spinophyllin-PP1 interaction are therefore useful for the treatment or prevention of psychosis or depressions.

Dimerized hydroxyphenylundecane of the formula

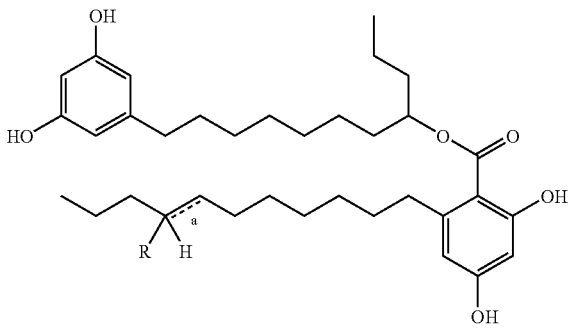

wherein
when "a" represents a single bond, R is —OH or —OC(O)$CH_3$, and
when "a" represents a double bond, R is absent, have been described as HIV integrase inhibitors in UK patent application GB 2327674.

SUMMARY OF THE INVENTION

It has now been found that the microorganism *Cryphonectria parasitica*, ST 002447 (DSM 14453), produces novel compounds which inhibit the spinophilin —PP1 interaction.

The present invention accordingly relates to compounds of the formula (I)

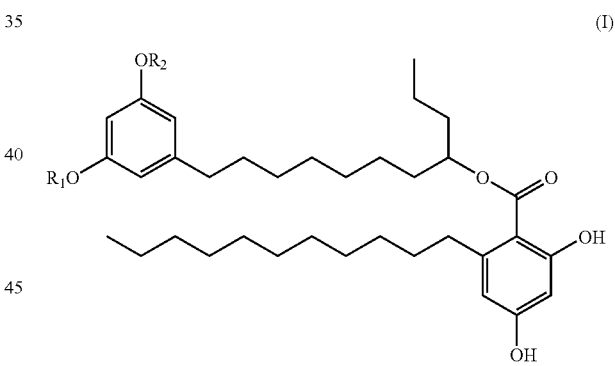

wherein
$R_1$ and $R_2$ are independently H or $SO_3H$, and/or a physiologically tolerated salts thereof and/or an obvious chemical equivalent.

In the compound of the formula (I), chiral centers may have the R or S configuration. The invention comprises optical pure compounds of the formula (I) as well as mixtures of stereoisomers in any ration.

Compounds of the formula (I) are subsequently also named as Spinosulfates.

In one embodiment $R_1$ and $R_2$ are $SO_3H$. A compound of the formula (I) having this combination of substituents is subsequently named Spinosulfate A.

A further embodiment is a compound of the formula (I) wherein $R_1$ and $R_2$ are H. This compound is subsequently named Spinosulfate B.

DETAILED DESCRIPTION OF THE INVENTION

Compounds of the formula (I) are obtainable by cultivation of the fungus *Chryphonectria parasitica* ST 002447 (DSM 14453). The said microorganism has been deposited on the 29 Aug. 2001 with the German Collection of Microorganisms and Cell Cultures (DSMZ—Deutsche Sammlung von Mikroorganismen und Zellkulturen GmbH), Braunschweig, Germany and has been given the accession number DSM 14453.

The invention relates to a compound of the formula (I) or a physiologically tolerated salt and/or an obvious chemical equivalent thereof, i.e. the compound Spinosulfate A or the compound Spinosulfate B, obtainable by cultivating *Cryphonectria parasitica*, DSM 14453 or one of its variants or mutants.

Thus, the present invention further relates to a process for the preparation of a compound of the formula (I) or a physiologically tolerated salt and/or an obvious chemical equivalent thereof, i.e. the compound Spinosulfate A or the compound Spinosulfate B, characterized in cultivating *Cryphonectria parasitica*, DSM 14453 or one of its variants or mutants, isolating and optionally purifying compound of the formula (I), and converting where appropriate into a physiologically tolerated salts or an obvious chemical equivalent.

The nutrient medium preferably contains one or more sources of carbon, nitrogen and nutrient inorganic salts, and optionally nutrient inorganic salts and/or trace elements. The carbon sources are, for example, oatmeal, starch, glucose, sucrose, dextrin, fructose, molasses, glycerol, lactose or galactose, preferably oatmeal. The sources of nitrogen are, for example, soyabean meal, peanut meal, yeast extract, beef extract, peptone, malt extract, corn steep liquor, gelatin or casamion acids, preferably corn steep liquor. The nutrient inorganic salts are, for example, sodium hydrogen phosphate, potassium hydrogen phosphate, ammonium hydrogen phosphate, sodium chloride, calcium chloride. Trace elements are, for example, Fe, Mn, Cu, B, Mo, Zn in the form of a salt or an acid or base.

In place of the strain DSM 14453, it is also possible to employ its mutants and variants as long as they produce the novel compound. A mutant refers to a microorganism in which some gene on the genome is modified, leaving the gene or genes responsible for the organism's ability to produce the compounds of formula (I) in recoverable amounts functional and heritable. Such mutants can be generated in a manner known in the art, for example irradiation, such as with ultraviolet or X-rays, or chemical mutagens such as, for example, ethyl methanesulfonate (EMS); 2-hydroxy-4-methoxybenzophenone (MOB) or N-methyl-N'-nitro-N-nitrosoguanidine (MNNG) or as described by Brock et al. in "Biology of Microorganisms" Prentice Hall, pages 238–247 (1984).

A variant refers to a phenotype of the microorganism. Microorganisms have the ability to adapt to environmental changes. This adaptive capacity is the reason for the observed physiological flexibility. In phenotypic adaptation, all cells of a population are involved. This type of change is not genetically conditioned. It is a modification that under altered conditions is reversible (H. Stolp, Microbial ecology: organisms, habitats, activities. Cambridge University Press, Cambridge, GB, Seite 180, 1988).

The screening for mutants and variants which produce the novel antibiotic can take place by determinating the biological activity of the active substance accumulated in the culture broth, for example by determining the antibiotic effect, or by detecting compounds that are known to be active in the culture broth by e.g. HPLC or LC-MS methods.

The cultivation of *Chryphonectria parasitica*, DSM 14453 may be carried out at temperatures between 15° C. and 35° C. and pH between 2.5 and 8.0, preferably under aerobic conditions. Preferably *Chryphonectria parasitica*, DSM 14453 is cultivated at 25° C. (±1° C.) and pH 3–6.

The cultivation of *Chryphonectria parasitica*, DSM 14453 is preferably carried out for 72–200 hours when an optimal yield of a Spinosulfate is obtained. It is particularly preferred to carry out the cultivation by fermentation for 96–144 hours under submerged conditions for example in shake flasks as well as in laboratory fermenters. The progress of fermentation and formation of a Spinosulfate can be detected by High Pressure Liquid Chromatography (HPLC) or LC-MS and by measuring the bioactivity of the culture broth. In the resulting culture broth the Spinosulfate is present in the culture filtrate as well as in the mycelium. It can be isolated using known separation techniques. Thus, it can be recovered from the culture filtrate by extraction with a water immiscible solvent such as ethyl acetate, dichloromethane, chloroform or butanol at pH 3–8 or by hydrophobic interaction chromatography using polymeric resins such as "Diaion HP-20®" or "MCI® Gel CHP-20P" (Mitsubishi Chemical Industries Limited, Japan), "Amberlite XAD®" (Rohm and Hass Industries U.S.A.), activated charcoal or ion exchange chromatography at pH 3–8. The preferred method is chromatography on MCI® Gel CHP-20P. The active material can also be recovered from mycelium by extraction with a water miscible solvent such as methanol, acetone, acetonitrile, n-propanol or isopropanol or a water immiscible solvent such as ethyl acetate, dichloromethane, chloroform or butanol at pH 3–8 and the preferred method is the extraction with methanol. Concentration and lyophilization of the extracts gives the active crude material.

Compounds of the formula (I) may, for example, be recovered from the crude material as follows:

By fractionation using any of the following techniques: normal phase chromatography (using alumina or silica gel as stationary phase and eluents such as petroleum ether, ethyl acetate, methylene chloride, acetone, chloroform, methanol or combinations thereof and additions of amines such as $NEt_3$), reverse phase chromatography (using reverse phase silica gel like dimethyloctadecylsilylsilica gel, also called RP-18 or dimethyloctylsilyl silica gel also called RP-8 as stationary phase and eluents such as water, buffers i.e. containing phosphate, acetate, citrate (pH 2–8) and organic solvents such as methanol, acetonitrile, acetone, tetrahydrofuran or combinations of these solvents), gel permeation chromatography using resins such as Sephadex® LH-20 (Pharmacia Chemical Industries, Sweden), TSKgel Toyopearl® HW (TosoHaas, Tosoh Corporation, Japan) in solvents such as methanol, chloroform, acetone, ethyl acetate or their combinations or Sephadex® G-10 and G-25 in water; or by counter-current chromatography using a biphasic eluent system made up of two or more solvents such as water, methanol, ethanol, iso-propanol, n-propanol, tetrahydrofuran, acetone, acetonitrile, methylene chloride, chloroform, ethyl acetate, petroleum ether, benzene and toluene. These techniques may be used repeatedly or a combination of the different techniques may be used. The preferred method is chromatography over reverse phase silica gel (RP-18).

Obvious chemical equivalents of the compound according to the invention are compounds which show slight chemical difference, and have the same effect or are converted under mild conditions into the compounds according to the invention. Said equivalents include, for example, esters, ethers, complexes or adducts of the or with a compound of the formula (I). Obvious chemical equivalents, such as ethers and/or esters of the compound of the formula (I), can be prepared by standard procedures known to one skilled in the art, for examples described in J. March, Advanced Organic Chemistry, John Wiley & Sons, 4$^{th}$ edition, 1992.

The compounds according to the present invention may be converted into pharmaceutically acceptable salts. The salts can be prepared by standard procedures known to one skilled in the art.

Physiologically tolerated salts of a compound of the formula (I) can be an organic and an inorganic salt and can be prepared as described in Remington's Pharmaceutical Sciences (17$^{th}$ edition, page 1418 (1985)). Salts like sodium and potassium salts, for example, may be prepared by treating the compounds according to the invention with suitable sodium or potassium bases.

The compounds according to the present invention and/or its pharmaceutically acceptable salts and obvious chemical equivalents can be administered to animals, preferably to mammals, and in particular to humans as pharmaceuticals on their own, in mixtures with one another and in the form of pharmaceutical compositions which permit parenteral administration. Accordingly, the present invention also relates to the use of a compound of the formula (I) or a pharmaceutically tolerated salt or a obvious chemical equivalent thereof, i.e. the compound Spinosulfate A or the compound Spinosulfate B, as pharmaceuticals, in particular for use as inhibitors of the spinophilin-PP1 complex and/or c-Jun N-terminal Kinase (JNK3), and are thus useful for the treatment and/or prevention of Alzheimer's Disease, Parkinson's Disease, Huntington's Diseases, stroke, psychosis and/or depressions.

The present invention further relates to a pharmaceutical comprising at least one compound of the formula (I) or a pharmaceutically tolerated salt or an obvious chemical equivalent thereof, i.e. the compound Spinosulfate A or the compound Spinosulfate B, and at least one pharmaceutically acceptable excipient.

The compounds according to the invention can be administered orally, intramuscularly, intravenously or by other modes of administration. Pharmaceutical compositions which contain these compounds or a physiologically tolerated salt or an obvious chemical equivalent thereof, optionally with other pharmaceutically active substances, can be prepared by mixing at least one compound of the formula (I) with at least one pharmacologically acceptable auxiliary. The mixture can then be converted into a suitable pharmaceutical form such as tablets, coated tablets, capsules, granules, powders, emulsions, suspensions or solutions.

Examples of pharmaceutically acceptable excipients are fillers, emulsifiers, lubricants, masking flavours, colorants and buffer substances tragacanth, lactose, talc, agar-agar, polyglycols, ethanol and water. Suitable and preferred for parenteral administration are suspensions or solutions in water. It is also possible to administer the active substances as such, without vehicles or diluents, in a suitable form, for example, in capsules.

The invention also relates to a method for the production of a pharmaceutical characterized in converting at least one compound of the formula (I) or a physiologically tolerated salt and/or an obvious chemical equivalent thereof, i.e. the compound Spinosulfate A or the compound Spinosulfate B, with at least one pharmaceutically acceptable excipient into a suitable dosage form.

As is customary, the galenic formulation and the method of administration as well as the dosage range which are suitable in a specific case depend on the species to be treated and on the state of the respective condition or disease and can be optimized using methods known in the art.

The following are illustrative examples of the present invention without limiting its scope thereof:

EXAMPLE 1

Maintenance of the Culture *Chryphonectria parasitica*, DSM 14453 a) Maintenance Medium

After dissolving the ingredients thoroughly by heating, the resultant solution was sterilized at 121° C. for 20 min and distributed in Petri dishes (15 mL/dish). After solidification the plates were inoculated with the start culture and incubated at 25° C. until good growth was observed. The well grown cultures were used for the following conservation steps.

| Maintenance medium: | |
|---|---|
| Malt extract | 2.00% |
| Yeast extract | 1.00% |
| Glucose | 1.00% |
| $(NH_4)_2HPO_4$ | 0.05% |
| Agar-Agar | 2.00% | b) Conservation at −135° C.:

1.5 mL of a sterile 10% DMSO solution are poured into 2 mL cryo vials. From the maintenance agar plate a 2 cm$^2$ agar piece is added to the DMSO solution and stored at −135° C.

c) Conservation in Liquid Nitrogen:

1.5 mL of a sterile 50% glycerol solution are poured into 2 mL cryo vials. From the maintenance agar plate a 2 cm$^2$ agar piece was taken and added to the glycerol solution and then stored in liquid nitrogen.

EXAMPLE 2

Fermentation of *Chryphonectria parasitica*, DSM 14453 in Shake Flasks a) Preparation of Seed Culture in Shake Flasks The seed medium was distributed in 100 mL amounts in 300 mL shake flasks and autoclaved at 121° C. for 30 minutes. The flasks were cooled to room temperature and inoculated with 2 $cm^2$ agar pieces taken from a 6 day old agar plate culture or with the content of one conservation vial (−135° C. or liquid nitrogen). The incubation was carried out for 72 hours on a rotary shaker at 140 rpm and 25° C.

| Seed medium: | |
|---|---|
| Malt extract | 2.00% |
| Yeast extract | 0.20% |
| Glucose | 1.00% |
| $(NH_4)_2HPO_4$ | 0.05% |
| pH 6 | |

Production Conditions:

The production medium (see below) was distributed in 100 mL amounts in 300 mL shake flasks and autoclaved at 121° C. for 20 minutes. The flasks were cooled to room temperature and inoculated with 2 mL of 72 hours old seed culture. The incubation was carried out for 144 hours on a rotary shaker at 140 rpm and 25° C. The production of Spinosulfate A was determined by testing the bioactivity against the inhibition of the spinophilin-PP1 complex as described in Example 5 and by HPLC and LC-MS analysis.

| Production medium: | |
|---|---|
| Cornsteep liquid | 0.50% |
| Tomato paste | 4.00% |
| Oatmeal | 1.00% |
| Trace element solution | 1.00 mL |

| Trace element solution: | |
|---|---|
| $FeSO_4 \times 7H_2O$ | 0.1000% |
| $MnSO_4 \times H_2O$ | 0.1000% |
| $CuCl_2 \times 2H_2O$ | 0.0025% |
| $CaCl_2 \times 2H_2O$ | 0.0100% |
| $H_3BO_3$ | 0.0056% |
| $(NH_4)_6Mo_7O_{24} \times 4H_2O$ | 0.0019% |
| $ZnSO_4 \times 7H_2O$ | 0.0200% |

EXAMPLE 3

Cultivation of A Culture of *Chryphonectria parasitica*, DSM 14453 in Fermenters (12 L)

Preparation of Seed Culture in Shake Flasks:

The seed medium was distributed in 500 mL amounts in 2 L Erlenmeyer flasks and autoclaved at 120° C. for 30 min The seed culture was grown in these flasks as described in Example 2.

Large Scale Fermentation:

8 L of the production medium in 12 L fermenter along with 1 ml/l L of Desmophen® as antifoaming agent was sterilized in situ for 45 min at 121° C., cooled to 25° C. (±1° C.) and seeded with 0.5 L (6.25% of 12 L fermenter) of the seed culture mentioned above.

The fermentation was run with the following parameters:

| | |
|---|---|
| Temperature: | 25° C. |
| Agitation: | 200 rpm |
| Aeration: | 0.5 vvm |
| Harvest time: | 96 h |

The production of Spinosulfates was determined by testing the inhibition as described in Example 8 and 9. The culture broth was harvested and centrifuged and the compounds Spinosulfate A and B were isolated and purified from the culture filtrate and the mycelium by the methods described in the Examples 4 and 6.

EXAMPLE 4

Isolation and Purification of Spinosulfate A

The culture broth (7.5 L) was centrifuged and the culter filtrate and the mycelium was freeze dried seperately. The lyophilization product of the mycelium was extracted with methanol (7 L) and the active extracts were pooled and concentrated under reduced pressure and freeze dried to yield 38 g of crude material. This material was purified by preparative HPLC using the following conditions:

| | | | |
|---|---|---|---|
| Column: | MCl ® Gel CHP-20P (260 × 50 mm; Kronlab) | | |
| Eluent: | A) $H_2O$ | | |
| | B) MeOH | | |
| Gradient: | min | % A | % B |
| | 0 | 90 | 10 |
| | 50.1 | 80 | 20 |
| | 65.1 | 60 | 40 |
| | 95.1 | 40 | 60 |
| | 125.1 | 20 | 80 |
| | 162.6 | 0 | 100 |
| | 193 | 0 | 100 |
| Flow: | 20 mL/min | | |
| Detection: | 210 nm | | |

The active fractions eluted after 125 min. The pooled fractions were concentrated under reduced pressure and freeze dried.

Final purification was done by preparative HPLC using the following conditions:

| | | | |
|---|---|---|---|
| Column: | Luna ® C18 (2) (5 μm, 250 × 21 mm; Phenomenex, Inc.) | | |
| Eluent: | A) 100% $H_2O$ | | |
| | B) 100% $CH_3CN$ | | |
| Gradient: | min | % A | % B |
| | 0 | 70 | 30 |
| | 10 | 70 | 30 |
| | 45 | 5 | 95 |
| Flow Rate: | 30 mL/min | | |
| Detection: | 210 nm | | |

The active fractions were analyzed by HPLC and LC-MS. The Spinosulfate A (MW: 730 Da) containing fractions eluted after 18 min (A). The pooled fractions were concentrated under reduced pressure and freeze dried. The overall yield from 7.5 L culture broth was 35 mg.

EXAMPLE 5

Physico Chemical and Spectral Properties of Spinosulfate A

Physico Chemical Properties of Spinosulfate A:

| | | |
|---|---|---|
| Appearance: | colorless oil | |
| Solubility: | Methanol, DMSO | |
| LC-MS: | Column: Purospher ® STAR RP.18e | |
| | (30 × 2 mm, 3 μm; Merck KgaA, Darmstadt) | |
| Eluent: | $CH_3CN$/10 mM $NH_4Ac$ (pH 4.5) | |
| Gradient: | time | % $CH_3CN$ |
| | 0.00 | 5.0 |
| | 6.00 | 100.0 |

-continued

| | |
|---|---|
| | 7.50    5.0 |
| | 9.00    100.0 |
| | 10.50    5.0 |
| | 13.00    5.0 |
| Flow: | 0.25 ml/min |
| Temp.: | 40° C. |
| Detection: | 210 nm, 230, 250, 320, 400 (UV); 100–2000 amu (MS) |
| Retention time: | 6.5 min |
| ESI-MS: | 729.5 amu (M—H)$^-$ |
| HR-ESI-MS: | 729.2987 [Calcd for $C_{35}H_{53}O_{12}S_2$: 729.2984 (M—H)$^-$] |
| Molecular formula: | $C_{35}H_{54}O_{12}S_2$ |
| MS$^n$-Experiments: | FTICR instrument, Bruker APEX III, 7T equipped with an external ESI-source |
| ESI$^-$: | 729 amu (M—H)$^-$ to 649 amu (—SO$_3$), 649 amu to 369 amu, 359 amu (—$C_{18}H_{26}O_3$), 341 (—$C_{18}H_{28}O_4$), 307 amu (—$C_{17}H_{26}O_5$S), 289 amu (—$C_{17}H_{28}O_6$S) |

TABLE 1

$^1$H- and $^{13}$C NMR Spectroscopic Data and HMBC Correlations of Spinosulfate A in CDCl$_3$ at 275 K.

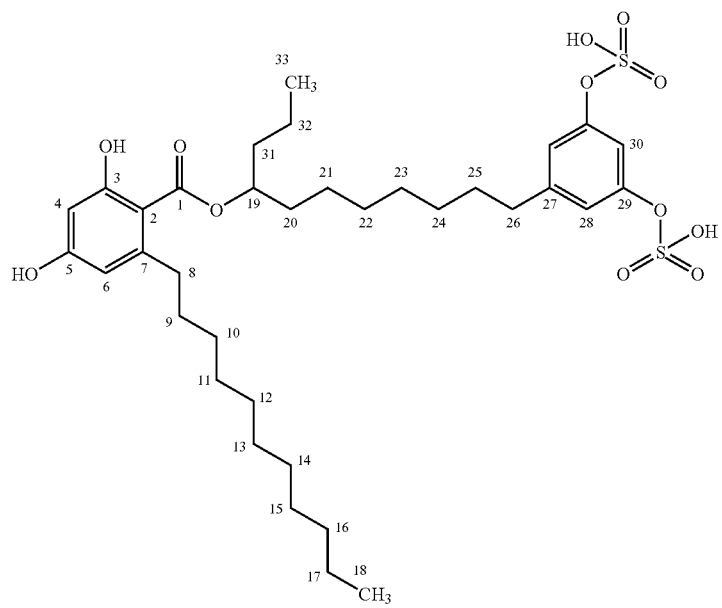

| Position | $^{13}$C δ (ppm) | $^1$H δ (ppm) | HMBC-Correlations $^{13}$C → $^1$H |
|---|---|---|---|
| 1 | 169.25 | — | H19 |
| 2 | 109.02 | — | 3-OH, H4, H6, H8 |
| 3 | 159.71 | — | 3-OH, H4 |
| 3-OH | — | 10.48 s | — |
| 4 | 100.38 | 6.14 | 3-OH, H6 |
| 5 | 160.21 | — | H4, H6 |
| 5-OH | — | 9.75 s, br | — |
| 6 | 108.63 | 6.12 | H4, H8 |
| 7 | 144.32 | — | H8 |
| 8 | 34.41 | 2.55 | H6 |
| 9 | 31.33 | 1.45 | H8 |
| 10 | 29.13 | 1.23–1.32 | H8 |
| 11 | 28.80–28.99 | 1.23–1.32 | |
| 12 | 28.80–28.99 | 1.23–1.32 | |
| 13 | 28.80–28.99 | 1.23–1.32 | |
| 14 | 28.80–28.99 | 1.23–1.32 | |
| 15 | 28.80–28.99 | 1.23–1.32 | |
| 16 | 31.20 | 1.23 | (H11–H15), H18 |
| 17 | 22.00 | 1.25 | (H11–H15), H18 |
| 18 | 13.87 | 0.85 | |
| 19 | 74.23 | 5.04 | H20, H31, H32, H21 |
| 20 | 33.58 | 1.59 | H19, H31, H19 |
| 21 | 24.82 | 1.31, 1.35 | H19 |
| 22 | 28.60 | 1.23–1.32 | |
| 23 | 28.80–28.99 | 1.23–1.32 | |
| 24 | 28.80–28.99 | 1.23–1.32 | H26 |
| 25 | 30.81 | 1.50 | H26 |

TABLE 1-continued

¹H- and ¹³C NMR Spectroscopic Data and HMBC Correlations of Spinosulfate A in CDCl₃ at 275 K.

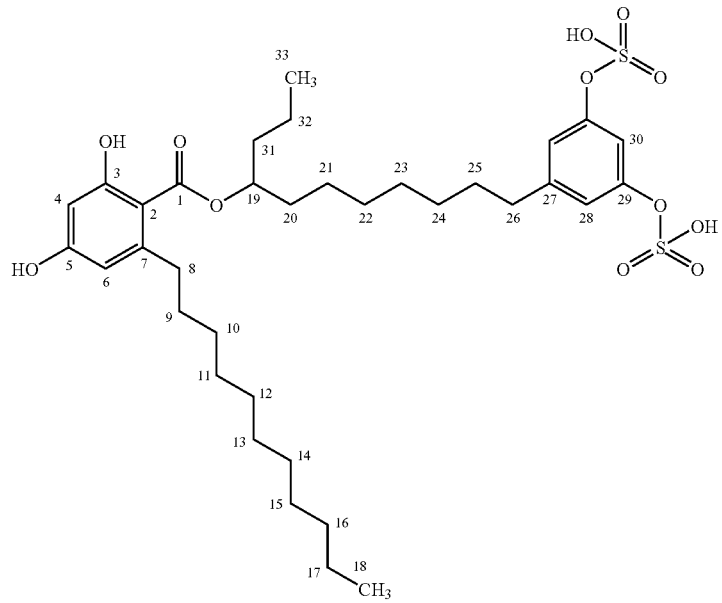

| Position | ¹³C δ (ppm) | ¹H δ (ppm) | HMBC-Correlations ¹³C → ¹H |
|---|---|---|---|
| 26 | 35.23 | 2.45 | H28 |
| 27 | 142.54 | — | H26 |
| 28 | 114.85 | 6.72 | H30, H28, H26 |
| 29 | 153.56 | — | H30, H28 |
| 30 | 110.23 | 6.75 | H28 |
| 31 | 35.76 | 1.57 | H32, H33, H19 |
| 32 | 18.07 | 1.35 | H31, H33, H19 |
| 33 | 13.74 | 0.88 | H31, H32 |

EXAMPLE 6

Isolation and Purification of Spinosulfate B

The culture broth (22 L) was separated and the mycelium (310 g) was first extracted with methanol (9 L) and afterwards with ethylacetate (4 L). The ethylactate fractions were combined and freeze dried to yield 9.4 g crude material. HPLC and LC-MS analysis revealed that the ethylacetate extract contained most of the active component and was thus purified by preparative HPLC using the following conditions:

| Column: | MCI ® Gel CHP-20P (260 × 50 mm; Kronlab) | | |
|---|---|---|---|
| Eluent: | A) H₂O | | |
| | B) Isopropanol | | |
| Gradient: | min | % A | % B |
| | 0 | 80 | 20 |
| | 15.1 | 60 | 40 |
| | 45.1 | 40 | 60 |
| | 75.1 | 20 | 80 |
| | 113 | 0 | 100 |
| | 142.5 | 0 | 100 |
| Flow: | 20 mL/min | | |
| Detection: | 210 nm | | |

The active fractions eluted after 100 min. The fractions were analyzed by HPLC and and LC-MS. The Spinosulfate containing fractions were pooled and concentrated under reduced pressure and freeze dried.

Final purification was done by preparative HPLC using the following conditions:

| Column: | Luna ® C18 (2) (5 µ, 250 × 21.20 mm; Phenomenex, Inc.) | | |
|---|---|---|---|
| Eluent: | A) 0.05% TFA in H₂O | | |
| | B) CH₃CN | | |
| Gradient: | min | % A | % B |
| | 0 | 95 | 5 |
| | 30 | 50 | 50 |
| | 75 | 0 | 100 |
| | 123 | 0 | 100 |
| Flow Rate: | 25 mL/min | | |
| Detection: | 210 nm | | |

The active fractions were analyzed by LC-MS. The Spinosulfate B containing fractions eluted after 60 min. The pooled fractions were concentrated under reduced pressure and freeze dried. The overall yield from 22 L culture broth was 60 mg.

EXAMPLE 7

Physico Chemical and Spectral Properties of Spinosulfate B

Appearance, solubility and LC-MS conditions are identical those described in Example 5.

| | |
|---|---|
| Retention time: | 8.5 min |
| ESI-MS: | 569.3 amu (M-H)⁻ |
| HR-ESI-MS: | 571.39885 [Calcd for $C_{35}H_{55}O_6$: 571.39932 (M-H)⁻] |
| Molecular formula: | $C_{35}H_{54}O_6$ |
| MSⁿ-Experiments: | FTICR instrument, Bruker APEX III, 7T equipped with an external ESI-source |
| ESI⁻: | 569 amu (M-H)⁻ to 289 amu, 245 amu, 91 amu; 289 amu to 245 amu. |

TABLE 2

$^1$H and $^{13}$C Spectroscopic Data of Spinosulfate B in DMSO at 300 K.

| | $^1$H δ (ppm) | $^{13}$C δ (ppm) |
|---|---|---|
| 1 | — | 169.31 |
| 2 | — | 108.75 |
| 3 | — | 159.89 |
| 4 | 6.14 | 100.39 |
| 5 | — | 160.37 |
| 6 | 6.12 | 108.75 |
| 7 | — | 144.43 |
| 8 | 2.55 | 34.49 |
| 9 | 1.45 | 31.39 |
| 10 | 1.26 | 29.19 |
| 11–15 | 1.25 | 28.91–28.62 |
| 16 | 1.25 | 31.22 |
| 17 | 1.25 | 22.02 |
| 18 | 0.84 | 13.87 |
| 19 | 5.05 | 74.19 |
| 20 | 1.58 | 33.59 |
| 21 | 1.33/1.29 | 24.84 |
| 22–24 | 1.25 | 28.91–28.62 |
| 25 | 1.46 | 30.67 |
| 26 | 2.34 | 35.25 |
| 27 | — | 144.08 |
| 28 | 6.00 | 106.20 |
| 29 | — | 158.11 |
| 30 | 6.00 | 99.91 |
| 31 | 1.56 | 35.78 |
| 32 | 1.39/1.33 | 18.08 |
| 33 | 0.88 | 13.75 |

EXAMPLE 8

JNK3 Assay

The assay was performed on a Cybio pipetting system in the 384-well plate format. The final assay volume was 30 µl, comprising 10 µl of a probe (an extract or a pure substance-to-be-tested), 10 µl of an enzym-subtrate mixture (JNK-3/GST-ATF2) and 10 µl ATP solution. After 20 min incubation at 37° C. 50 µl HTRF abtibody mixture (XL665-anti-GST/(Eu)cryptat anti-P-ATF2) were added. The emission intensity of the energy transfer and of Eu at 665 and 615 nm, resp., were measured after 120 min at room temperature and stimulation of the probes at 340 nm in a Victor2® (Wallac).

Buffer I for diluting JNK3, GST-ATF2, ATP:

| | |
|---|---|
| 25 mM | HEPES, pH 7.5 |
| 100 µM | $MgCl_2$ |
| 0.03% | TRITON X 100 |
| 10 mM | DTT |
| 5% | glycerol |

Buffer II for diluting HTRF reagents:

| | |
|---|---|
| 100 mM | HEPES, pH 7.0 |
| 100 mM | KF |
| 133 mM | EDTA |
| 1 g/l | BSA |

| Further reagents: | | |
|---|---|---|
| JNK3 Kinase | Biotech, Vitry | 8 ng/well |
| GST-ATF2 | Biotech, Vitry | 88 ng/well |
| ATP solution | Sigma, A7699 | 15 µM |
| Anti-GST-XL665 | CisBio | 125 ng/well |
| Anti-P-ATF2-(Eu)cryptate | NEB/CisBio | 6 ng/well |

Each plate included 16 positiv controls (maximum energy transfer, buffer I instead of probe), 8 blank controls (minimal energy transfer, buffer 11 instead of ATP) and 8 wells containing a 200 µM EDTA solution.

The results were calculated as follows:

Signal Ration:

$SR = (\text{intensity}(665 \text{ nm})/\text{intensity}(615 \text{ nm}))$

Blank Correction:

$\text{Delta } F(\%) = (SR(\text{Probe}) - SR(\text{min}))/(SR(\text{min}) \times 100)$ Inhibition:

$\text{Inhibition }(\%) = 100 \times [1-(\text{Delta } F(\text{Probe})/\text{Delta } F(\text{max}))$ The following $IC_{50}$ values for Spinosulfate A and B have been found:

Spinosulfate A: $IC_{50}$=0,5 µM,

Spinosulfate B: $IC_{50}$=10 µM.

EXAMPLE 9

PP1 Assay

The assay was performed on a Cybio pipetting system in the 384-well plate format. The final assay volume was 55 µl.

Plate Coating:

Elisa high binding plates (greiner) were coated by adding 30 µl spinophilin (10 µg/ml) to each well. Low controls received 30 µl BSA (1%) instead. After an overnight incubation at 4° C. the plates were washed 3 times with TBS wash buffer (20 mM TRIS/HCl, pH 7.5, 500 mM NaCl) before they were used in the assay.

Quantification of the Protein-Protein Interaction by DELFIA®:

50 µl of GST-pp1 diluted in TBS buffer (1.25 µg/ml) was added to each well on the coated plates. After the addition of 5 µl of appropriately diluted test sample (or TBS in low and high controls) the plates were incubated at room temperature for 3 hours. After a washing step (3 times with 80 µl TBS/well) there were 30 µl of a Eu labeled antibody (Eu-W 1024-anti-GST-antibody, 0.1 µg/mL in Delfia assay buffer supplemented with 0.5% BSA) added to each well. After a further incubation (1 hour at room temperature) and washing (3×80 µl TBS/well) there were 50 µl of an enhancer solution (Wallac) added to each well. Subsequently, the plates were incubated for 30 minutes at room temperature before the TRF signal is read at 615 nm in a Victor Wallac plate reader.

For result evaluation the data were first blanc-corrected. Thereafter, the activity of the samples was calculated in relation to the high controls by using the following equation:

$$100\times[1-(\text{TRF signal at 615nm}_{mean\ sample}/\text{TRF signal at 615nm}_{mean\ control}]$$

The $IC_{50}$ value of Spinosulfate A was determined as 34 µM, the $IC_{50}$ value of Spinosulfate B as 10 µM.

The invention claimed is:

1. A compound of the formula (I)

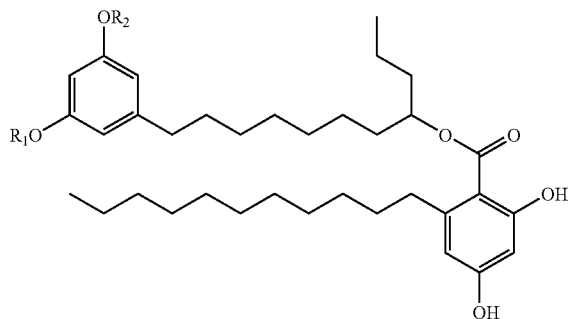

(I)

wherein $R_1$ and $R_2$ are independently H or $SO_3H$, and/or a physiologically tolerated salt thereof.

2. The compound according to claim 1, wherein $R_1$ and $R_2$ are $SO_3H$.

3. The compound according to claim 1, wherein $R_1$ and $R_2$ are H.

4. The compound according to claim 1, obtained by cultivating *Cryphonectria parasitica*, DSM 14453.

5. The compound according to claim 1, of the molecular formula $C_{35}H_{54}O_{12}S_2$ and further characterized by the $^1H$ NMR data (δ in ppm) 0.85, 0.88, 1.23, 1.23–1.32, 1.25, 1.31, 1.45, 1.50, 1.57, 1.59, 2.45, 2.55, 5.04,6.12, 6.14, 6.72, 6.75, 9.75, 10.48 and by the $^{13}C$ NMR data (δ in ppm) 13.74, 13.87, 18.07, 22.00, 24.82, 28.60, 28.80–28.99, 29.13, 30.8, 31.20, 31.33, 33.58, 34.41, 35.23, 35.76, 74.23, 100.38, 108.63, 109.02, 110.23, 114.85, 142.54, 144.32, 153.56, 159.71, 160.21, 169.25.

6. The compound according to claim 1, of the molecular formula $C_{35}H_{54}O_6$ and further characterized by the $^1H$ NMR data (δ in ppm) 0.84, 0.88, 1.25, 126, 1.33/1.29, 1.39/1.33, 1.45. 1.46, 1.56, 1.58, 2.34, 2.55, 5.05, 6.00, 6.12, 6.14 and by the $^{13}C$ NMR data (δ in ppm) 13.75, 13.87, 18.08, 22.02, 24.84, 28.91–28.62, 28.91–28.62, 29.19, 30.67, 31.22, 31.39, 33.59, 34.49,35.25, 35.78, 74.19, 99.91, 100.39, 106.20, 108.75, 144.08, 144.43, 158.11, 159.89, 160.37, 169.31.

7. A process for the preparation of a compound according to claim 1, comprising: (a) cultivating *Cryphonectria parasitica*, DSM 14453, (b) isolating and optionally purifying compound of the formula (I), and (c) optionally converting into a physiologically tolerated salt.

8. A pharmaceutical composition, comprising at least one compound according to claim 1, and at least one pharmaceutically acceptable excipient.

9. A method for the production of a pharmaceutical composition as claimed in claim 8, characterized in converting at least one compound according to claim 1 with at least one pharmaceutically acceptable excipient into a suitable dosage form.

10. The isolated microorganism strain: *Cryphonectria parasitica*, DSM 14453.

* * * * *